United States Patent
Viswanathan

(10) Patent No.: US 7,831,294 B2
(45) Date of Patent: Nov. 9, 2010

(54) SYSTEM AND METHOD OF SURGICAL IMAGINING WITH ANATOMICAL OVERLAY FOR NAVIGATION OF SURGICAL DEVICES

(75) Inventor: Raju R. Viswanathan, St. Louis, MO (US)

(73) Assignee: Stereotaxis, Inc., St. Louis, MO (US)

(*) Notice: Subject to any disclaimer, the term of this patent is extended or adjusted under 35 U.S.C. 154(b) by 1334 days.

(21) Appl. No.: 10/962,174

(22) Filed: Oct. 7, 2004

(65) Prior Publication Data
US 2006/0079745 A1 Apr. 13, 2006

(51) Int. Cl.
*A61B 5/05* (2006.01)
(52) U.S. Cl. .................. 600/425; 600/424; 600/429; 378/20; 378/21; 378/29
(58) Field of Classification Search ......... 600/424–429, 600/407, 300; 378/20, 21, 29, 143, 144
See application file for complete search history.

(56) References Cited

U.S. PATENT DOCUMENTS

| | | | |
|---|---|---|---|
| 5,654,864 A | | 8/1997 | Ritter et al. |
| 5,713,357 A | * | 2/1998 | Meulenbrugge et al. .... 600/411 |
| 5,931,818 A | | 8/1999 | Werp et al. |
| 6,014,580 A | | 1/2000 | Blume et al. |
| 6,015,414 A | | 1/2000 | Werp et al. |
| 6,081,739 A | * | 6/2000 | Lemchen ..................... 600/407 |
| 6,128,174 A | | 10/2000 | Ritter et al. |
| 6,148,823 A | | 11/2000 | Hastings |
| 6,152,933 A | | 11/2000 | Werp et al. |
| 6,157,853 A | | 12/2000 | Blume et al. |
| 6,212,419 B1 | | 4/2001 | Blume et al. |
| 6,241,671 B1 | | 6/2001 | Ritter et al. |
| 6,292,678 B1 | | 9/2001 | Hall et al. |
| 6,296,604 B1 | | 10/2001 | Garibaldi et al. |
| 6,298,257 B1 | | 10/2001 | Hall et al. |
| 6,298,259 B1 | * | 10/2001 | Kucharczyk et al. ........ 600/411 |

(Continued)

FOREIGN PATENT DOCUMENTS

WO    WO 00/47103    8/2000

(Continued)

OTHER PUBLICATIONS

European Search Report for corresponding application No. EP05803625.2 Date: Mar. 11, 2009 pp. 7.

*Primary Examiner*—Brian Casler
*Assistant Examiner*—Joel M Lamprecht
(74) *Attorney, Agent, or Firm*—Harness, Dickey & Pierce, P.L.C.

(57) ABSTRACT

A system and method are provided for control of a navigation system for deploying a medical device within a subject, and for enhancement of a display image of anatomical features for viewing the projected location and movement of medical devices, and projected locations of a variety of anatomical features and other spatial markers in the operating region. The display of the X-ray imaging system information is augmented in a manner such that a physician can more easily become oriented in three dimensions with the use of a single-plane X-ray display. The projection of points and geometrical shapes within the subject body onto a known imaging plane can be obtained using associated imaging parameters and projective geometry.

72 Claims, 12 Drawing Sheets

U.S. PATENT DOCUMENTS

| | | | |
|---|---|---|---|
| 6,304,768 B1 | 10/2001 | Blume et al. | |
| 6,315,709 B1 | 11/2001 | Garibaldi et al. | |
| 6,330,467 B1 | 12/2001 | Creighton, IV et al. | |
| 6,352,363 B1 | 3/2002 | Munger et al. | |
| 6,364,823 B1 | 4/2002 | Garibaldi et al. | |
| 6,375,606 B1 | 4/2002 | Garibaldi et al. | |
| 6,385,472 B1 | 5/2002 | Hall et al. | |
| 6,401,723 B1 | 6/2002 | Garibaldi et al. | |
| 6,428,551 B1 | 8/2002 | Hall et al. | |
| 6,459,924 B1 | 10/2002 | Creighton, IV et al. | |
| 6,470,207 B1 | 10/2002 | Simon et al. | 600/426 |
| 6,505,062 B1 | 1/2003 | Ritter et al. | |
| 6,507,751 B2 | 1/2003 | Blume et al. | |
| 6,522,909 B1 | 2/2003 | Garibaldi et al. | |
| 6,524,303 B1 | 2/2003 | Garibaldi | |
| 6,527,782 B2 | 3/2003 | Hogg et al. | |
| 6,529,758 B2 * | 3/2003 | Shahidi | 600/407 |
| 6,535,756 B1 | 3/2003 | Simon et al. | 600/424 |
| 6,537,196 B1 | 3/2003 | Creighton, IV et al. | |
| 6,542,766 B2 | 4/2003 | Hall et al. | |
| 6,562,019 B1 | 5/2003 | Sell | |
| 6,630,879 B1 | 10/2003 | Creighton, IV et al. | |
| 6,662,034 B2 | 12/2003 | Segner et al. | |
| 6,677,752 B1 | 1/2004 | Creighton, IV et al. | |
| 6,702,804 B1 | 3/2004 | Ritter et al. | |
| 6,733,511 B2 | 5/2004 | Hall et al. | |
| 6,755,816 B2 | 6/2004 | Ritter et al. | |
| 6,817,364 B2 | 11/2004 | Garibaldi et al. | |
| 6,834,201 B2 | 12/2004 | Gillies et al. | |
| 6,902,528 B1 | 6/2005 | Garibaldi et al. | |
| 6,911,026 B1 | 6/2005 | Hall et al. | |
| 6,968,846 B2 | 11/2005 | Viswanathan | |
| 6,975,197 B2 | 12/2005 | Creighton, IV | |
| 6,980,843 B2 | 12/2005 | Eng et al. | |
| 7,008,418 B2 | 3/2006 | Hall et al. | |
| 7,010,338 B2 | 3/2006 | Ritter et al. | |
| 7,019,610 B2 | 3/2006 | Creighton, IV et al. | |
| 7,020,512 B2 | 3/2006 | Ritter et al. | |
| 7,066,924 B1 | 6/2006 | Garibaldi et al. | |
| 7,103,399 B2 * | 9/2006 | Miga et al. | 600/425 |
| 2001/0027263 A1 | 10/2001 | Zylka et al. | |
| 2001/0038683 A1 | 11/2001 | Ritter et al. | |
| 2002/0019644 A1 | 2/2002 | Hastings et al. | |
| 2002/0085681 A1 | 7/2002 | Jensen | |
| 2002/0177789 A1 | 11/2002 | Ferry et al. | |
| 2004/0006301 A1 | 1/2004 | Sell et al. | |
| 2004/0019447 A1 | 1/2004 | Shachar | |
| 2004/0064153 A1 | 4/2004 | Creighton, IV et al. | |
| 2004/0068170 A1 | 4/2004 | Wang et al. | 600/407 |
| 2004/0068173 A1 | 4/2004 | Viswanathan | |
| 2004/0096511 A1 | 5/2004 | Harburn et al. | |
| 2004/0133130 A1 | 7/2004 | Ferry et al. | |
| 2004/0157082 A1 | 8/2004 | Ritter et al. | |
| 2004/0157188 A1 | 8/2004 | Luth et al. | 433/75 |
| 2004/0158972 A1 | 8/2004 | Creighton, IV et al. | |
| 2004/0186376 A1 | 9/2004 | Hogg et al. | |
| 2004/0199074 A1 | 10/2004 | Ritter et al. | |
| 2004/0249262 A1 | 12/2004 | Werp et al. | |
| 2004/0249263 A1 | 12/2004 | Creighton, IV | |
| 2004/0260172 A1 | 12/2004 | Ritter et al. | |
| 2005/0020911 A1 | 1/2005 | Viswanathan et al. | |
| 2005/0043611 A1 | 2/2005 | Sabo et al. | |
| 2005/0065435 A1 | 3/2005 | Rauch et al. | |
| 2005/0096589 A1 | 5/2005 | Shachar | |
| 2005/0113628 A1 | 5/2005 | Creighton, IV et al. | |
| 2005/0113812 A1 | 5/2005 | Viswanathan et al. | |
| 2005/0119687 A1 | 6/2005 | Dacey, Jr. et al. | |
| 2005/0182315 A1 | 8/2005 | Ritter et al. | |
| 2005/0256398 A1 | 11/2005 | Hastings et al. | |
| 2006/0009735 A1 | 1/2006 | Viswanathan et al. | |
| 2006/0025679 A1 | 2/2006 | Viswanathan et al. | |
| 2006/0036125 A1 | 2/2006 | Viswanathan et al. | |
| 2006/0036163 A1 | 2/2006 | Viswanathan | |
| 2006/0041178 A1 | 2/2006 | Viswanathan et al. | |
| 2006/0041179 A1 | 2/2006 | Viswanathan et al. | |
| 2006/0041180 A1 | 2/2006 | Viswanathan et al. | |
| 2006/0041181 A1 | 2/2006 | Viswanathan et al. | |
| 2006/0041245 A1 | 2/2006 | Ferry et al. | |
| 2006/0058646 A1 | 3/2006 | Viswanathan | |
| 2006/0074297 A1 | 4/2006 | Viswanathan | |
| 2006/0079745 A1 | 4/2006 | Viswanathan | |
| 2006/0079812 A1 | 4/2006 | Viswanathan | |
| 2006/0093193 A1 | 5/2006 | Viswanathan | |
| 2006/0094956 A1 | 5/2006 | Viswanathan | |
| 2006/0100505 A1 | 5/2006 | Viswanathan | |
| 2006/0114088 A1 | 6/2006 | Shachar | |
| 2006/0116633 A1 | 6/2006 | Shachar | |
| 2006/0144407 A1 | 7/2006 | Aliberto et al. | |
| 2006/0144408 A1 | 7/2006 | Ferry | |

FOREIGN PATENT DOCUMENTS

| | | |
|---|---|---|
| WO | WO 02/065931 | 8/2002 |
| WO | WO 2004/021910 | 3/2004 |

* cited by examiner

SYSTEM AND METHOD OF SURGICAL IMAGING WITH ANATOMICAL OVERLAY FOR NAVIGATION OF SURGICAL DEVICES

FIELD OF THE INVENTION

This invention relates to a system and methods for interventional medicine, and more specifically to computer assisted navigation and imaging of medical devices within a subject body.

BACKGROUND OF THE INVENTION

Interventional medicine is the collection of medical procedures in which access to the site of treatment is made through one of the subject's blood vessels, body cavities or lumens. For example, angioplasty of a coronary artery is most often performed using a catheter which enters the patient's arterial system through a puncture of the femoral artery in the groin area. Other interventional medical procedures include the assessment and treatment of tissues on the inner surface of the heart (endocardial surfaces) accessed via peripheral veins or arteries, treatment of vascular defects such as cerebral aneurysms, removal of embolic clots and debris from vessels, treatment of tumors via vascular access, endoscopy of the intestinal tract, etc.

Interventional medicine technologies have been applied to manipulation of instruments which contact tissues during surgical procedures, making these procedures more precise, repeatable and less dependent of the device manipulation skills of the physician. Some presently available interventional medical systems for directing the distal tip of a medical device from the proximal end of the medical device use computer-assisted navigation and a display means for providing a visual display of the medical device along with anatomical images obtained from a separate imaging apparatus. Such systems can provide a visual display of blood vessels and tissues, obtained from a Fluoroscopy (X-ray) imaging system for example, and can display a projection of the medical device being navigated to a target destination using a computer that controls the orientation of the distal tip of the medical device.

In some cases, it may be difficult for a physician to become oriented in a three dimensional setting using a display of a single-plane X-ray image projection. Enhancement or augmentation of the single-plane X-ray image may be required to aid the physician in visualizing the orientation of the medical device and blood vessels. A method is therefore desired for enhancing a display image of the anatomical surfaces and the orientation of a medical device in real time to improve navigation through the blood vessels and tissues.

SUMMARY OF THE INVENTION

According to the principles of the present invention, a system and method are provided for control of a navigation system for deploying a medical device within a subject, and for enhancement of a display image of anatomical features for viewing the current location and orientation of a medical device moving through the subject body. The display of the X-ray imaging system information is augmented in a manner such that a physician can more easily become oriented in three dimensions with the use of a single-plane X-ray display. A typical X-ray imaging system comprises a source for emitting a beam through a three dimensional space and onto a plane, where a point within a subject body in the three dimensional space is projected onto the plane. The projection of a point within the subject body onto the imaging plane can be obtained using an orthographic projection matrix derived from the point-to-image plane distance and the source-to-image plane distance. Thus, a point location within the subject body having known coordinates, properly registered to the frame of reference of the X-ray system, can be projected onto the X-ray image plane of the live X-ray image in the same manner.

In accordance with one aspect of the invention, a method of projection can be used to graphically overlay a representation of the actual medical device location and orientation onto the X-ray image. One or more desired target points within the subject can also be projected onto the X-ray image, as well as one or more reference markers on the subject to track patient movement. A graphical representation of a virtual medical device can be overlaid to show a visual reference of a predicted new location and orientation of the actual medical device that corresponds to a desired navigational configuration. A mathematical model of the medical device can be used to define the configuration of the virtual medical device, which can model the behavior of the device corresponding to a change in navigation control variables to predict deflection and rotation of the medical device. A desired direction for steering the medical device within the plane of the X-ray image can be graphically represented, and surface shapes within the subject may also be rendered and graphically represented on the X-ray image display. All the graphically overlaid information is also updated in real time as the X-ray imaging system is rotated or moved, to augment the image display and enhance visualization of the orientation of a medical device in a three dimensional space using a single-plane X-ray image displayed on the control system.

It is thus an object of the invention to provide a system and method for augmenting the displayed anatomical image of a subject with graphically overlaid objects to provide enhanced visualization of medical devices, anatomical locations, shapes, markers, and other objects and annotations in a three dimensional space for aiding in the orientation and navigation of the medical device through the subject body.

It is a further object of the invention to provide a system and method for enabling virtual representation of the medical device, for providing a visual reference of a predicted orientation and location of the medical device corresponding to a desired configuration or movement to a desired target.

DETAILED DESCRIPTION OF THE INVENTION

Figure 1:
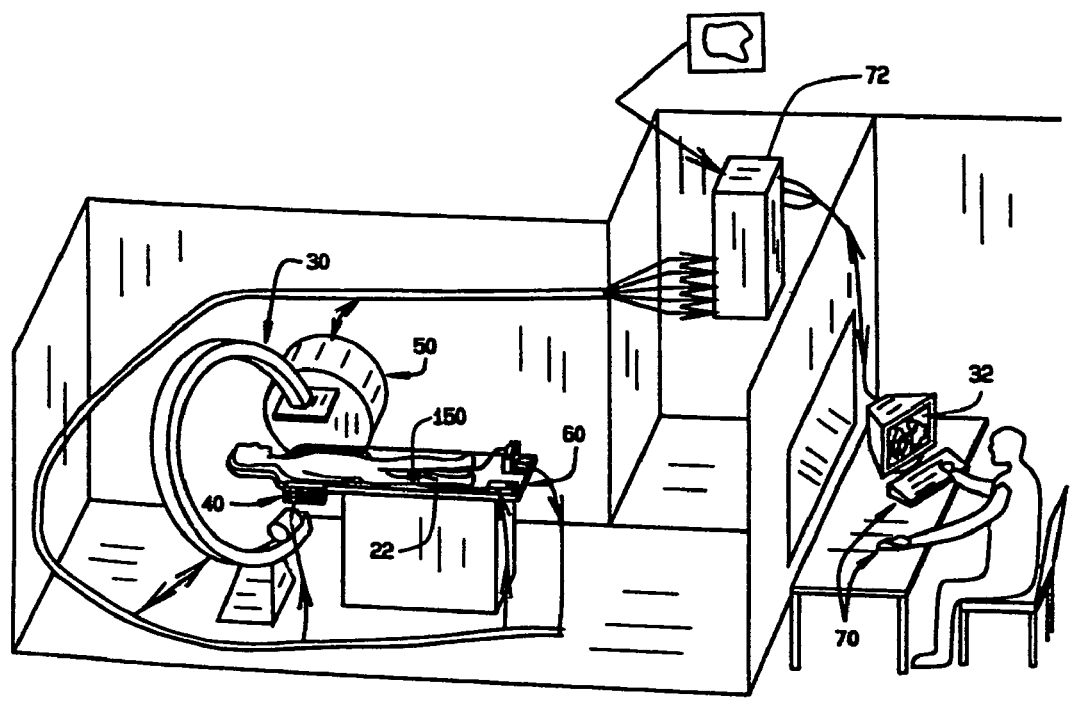
FIG. 1 is a schematic diagram of an automated system for navigating a medical device through the lumens and cavities in the operating regions in a patient in accordance with the principles of this invention.

An automated system for navigating a medical device through the lumens and cavities in an operating region in a patient in accordance with the principles of this invention is indicated generally as 20 in FIG. 1. The system 20 comprises an elongate medical device 22, having a proximal end and a distal end adapted to be introduced into the operating region in a subject. The system 20 also comprises an imaging system 30 for displaying an image of the operating region on a display 32, including a representation of the distal end of the medical device 22 in the operating region.

The system also includes a navigation system for manipulating the distal end of the medical device 22. In this preferred embodiment the navigating system is a magnetic navigation system 50. Of course, the navigation system could alternatively be a piezoelectric or electrostrictive system or a mechanical control system with pull wires or servo motors, or other suitable system for orienting the distal tip of the medical device. The magnetic navigation system 50 orients the distal end of the medical device 22 in a selected direction through the interaction of magnetic fields associated with the medical device 22 inside the operating region and at least one external source magnet outside the subject's body. The catheter may then be advanced in the selected direction, to reach the target destination through the successive reorientation stepwise process and advancement.

A preferred embodiment of the present invention describes a method for a navigation system associated with an elongate flexible catheter or medical device and an X-ray imaging system, for providing a suitable projection of a graphic overlay of the medical device and target locations within the subject body. The control or actuation means used to steer or navigate the medical device with a computer controlled navigation system may be any of a variety of method known to those skilled in the art, such as mechanical, magnetic, electrostrictive, hydraulic, or others. One preferred embodiment is one where an externally applied magnetic field is used to steer the device, while device advancement and retraction is mechanically driven. Such a navigation system is typically used in conjunction with an X-ray system such as a Fluoroscopy Imaging system, with a mutually known registration between the systems. Other anatomical features such as curves, ridge lines, ablation lines, surface portions, landmark locations, marker locations as reference, and so on, possibly including data from preoperative or intraoperative three dimensional images, can be overlaid on the live X-ray display. Past device configurations can also be displayed as a reference so that any changes in configuration such as patient shift can be monitored during the course of the procedure.

Likewise reconstructed features such as blood vessels reconstructed from contrast agent injection and subsequent imaging and image processing, or other path reconstructions as defined by a user to produce a three dimensional path could be overlaid on the live X-ray display.

Figure 2:
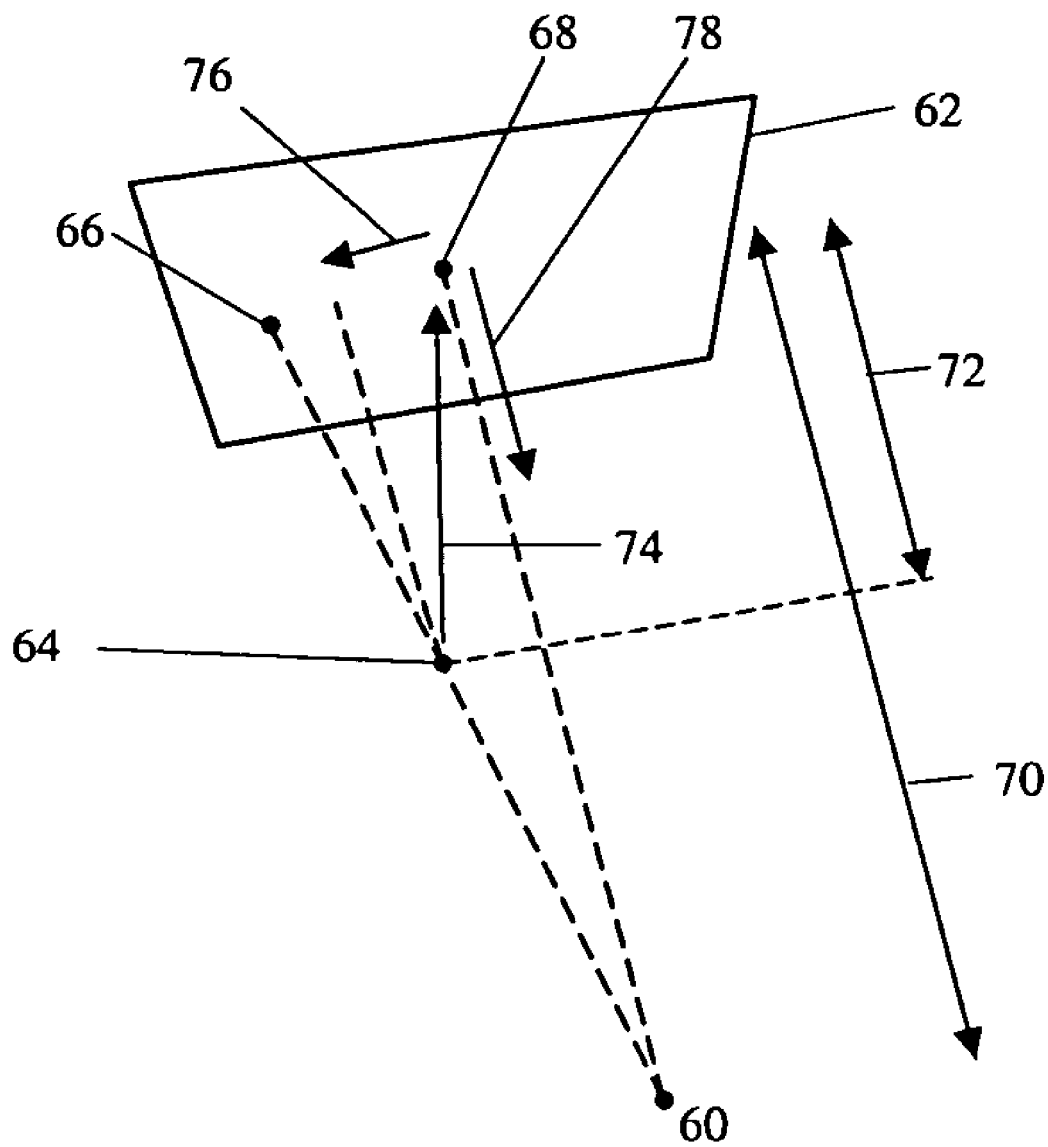
FIG. 2 is an illustration of the projection geometry for projecting a location point onto an imaging plane in accordance with the principles of the present invention.

A typical X-ray imaging system comprises a source for emitting a beam through a three dimensional space and onto an imaging plane, where a point within a subject body in the three dimensional space is projected onto the plane. In a preferred embodiment, the X-ray imaging system is preferably a Fluoroscopy imaging system capable of providing images on at least two separate planes, which together can provide the three dimensional coordinates for a location displayed in the two separate planes. FIG. 2 shows a geometric illustration of an X-ray source point of origin 60 for emitting a beam towards the subject and the imaging plane 62. The projection of $\vec{x}$, a point 64 in a three dimensional space, onto the imaging plane 62 as a perspective projection $\vec{x}_p$, can be obtained using an orthographic projection matrix. The orthographic projection matrix can be derived from h the point-to-image plane distance 72, and d the source-to-image plane distance 70, or distance to the center $\vec{x}_c$ of the plane 62. A vector $\vec{q}$ from a point in space $\vec{x}$ to the center of the plane $\vec{x}_c$ may be defined as $\vec{q} = (\vec{x} - \vec{x}_c)$:. The source-to-image distance 70 is defined as d. The orthographic projection of $\vec{q}$ onto the imaging plane 72 is:

$$\vec{y} = (I - nn^T)\vec{q} \text{ or}$$

$$\vec{y} = A\vec{q} = A(\vec{x} - \vec{x}_c)$$

where $nn^T$ is the 3×3 outer product constructed from the normal $\vec{n}$ to the X-ray image plane, I is the 3×3 identity matrix, and $(I-nn^T)$ is the orthographic projection matrix. From FIG. 2, it can be seen that:

$$\frac{|\vec{x}_P - \vec{x}_C|}{d} = \frac{|\vec{y}|}{(d-h)}, \text{ where } h = (\vec{q} \cdot \vec{n}) \qquad (1)$$

$$\text{Since } (\vec{x}_P - \vec{x}_C) = |\vec{x}_P - \vec{x}_C| \cdot \frac{\vec{y}}{|\vec{y}|}, \qquad (2)$$

Equation (1) may be rewritten as:

$$(\vec{x}_P - \vec{x}_C) = \frac{d}{(d-h)}\vec{y} = \frac{d}{(d-\vec{n}\cdot(\vec{x}-\vec{x}_C))}A(\vec{x}_P - \vec{x}_C) \qquad (3)$$

Equation (3) above defines the perspective projection $\vec{x}_p$ of point $\vec{x}$ onto the imaging plane, so $\vec{x}_p$ may be rewritten in the form:

$$\vec{x}_P = \vec{x}_C + \frac{d}{(d-\vec{n}\cdot(\vec{x}-\vec{x}_C))}A(\vec{x}_P - \vec{x}_C) \qquad (4)$$

Figure 3:
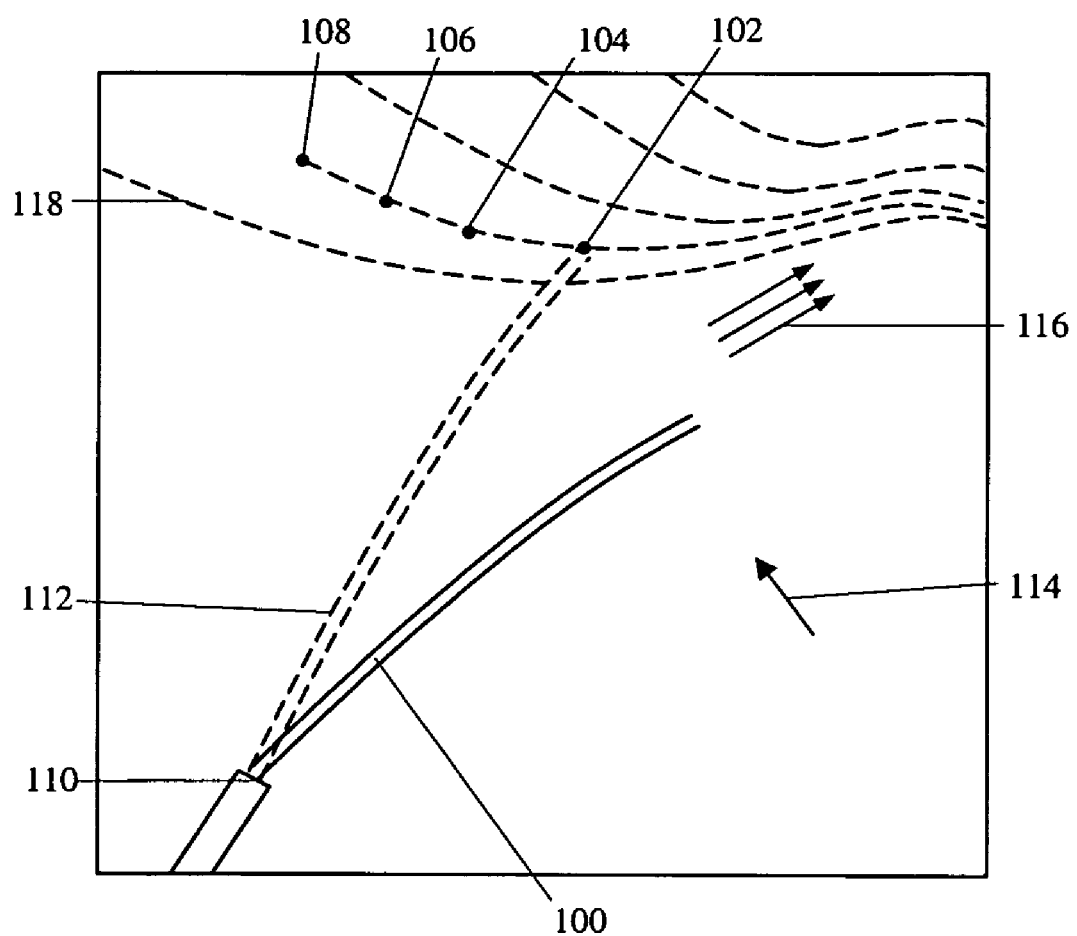
FIG. 3 is an illustration of an anatomical image display comprising images of the actual medical device, graphically overlaid images of a virtual medical device configuration and a series of target locations according to the principles of the present invention.

For any given point $\vec{x}$ in a three dimensional space, a corresponding perspective projection point $\vec{x}_p$ on the X-ray image plane can be determined using equation (4) above. Thus, for any point location within the imaging volume, a corresponding graphic overlay object may be suitably projected onto the X-ray image display. Such graphic overlay objects that may be suitably projected onto a display as illustrated in FIG. 3 may include objects such as the actual medical device 100 and target locations 102, 104, 106 and 108 within the operating region of the subject. Other objects that can be usefully overlaid on the live X-ray display include anatomical features such as curves, ridge lines, ablation lines, surface portions, landmark locations, marker locations used as reference, and so on, possibly including data from preoperative or intraoperative three dimensional images. Likewise, previously marked or identified device configurations can also be displayed as a reference so that any changes in configuration due to factors such as patient shift can be monitored during the course of the procedure. Additionally, reconstructed features such as blood vessels reconstructed from contrast agent injection and subsequent imaging and image processing, or other path reconstructions as defined by a user to produce a three dimensional path, or a variety of path-like or other features extracted from three dimensional image data could be overlaid on the live X-ray display.

As the Fluoroscopic imaging system is moved or rotated about the subject, the graphically overlaid objects may be continuously updated and displayed along with the continuously updated X-ray images to provide projection images in real time to improve visualization of the orientation of the medical device and target locations.

Other graphic overlay objects that can be suitably projected onto the display may include one or more reference markers 110 on the subject body to provide a reference for the movement of the medical device 100. In the preferred embodiment, the medical device 100 is preferably deployed from the distal end of a relatively stiff sheath inserted within the subject body. The distal end of such a sheath functions as a base for the distal end of a medical device 100 deployed therefrom.

One efficient method to mark the pivot or base of the medical device as a reference marker 110 is to position the tip of the medical device 110 at the intended base, for example at the distal tip of a sheath, and then record the current location of the tip as a reference marker, as illustrated in FIG. 3 at 110. Reference markers could also be used to indicate target locations for the tip of the medical device to access, and text or other graphic annotations could be used to distinguish and identify various locations. A pre-operative anatomical three-dimensional data set, of an endocardial surface for example, could also be graphically rendered and projected onto the display at 118, after a suitable registration of the coordinates to the frame of reference of the X-ray is performed. Likewise, an intra-operative three-dimensional data set could also be graphically rendered and projected onto the image display.

In the preferred embodiment where a magnetic navigation system is employed for controlling the orientation of the distal tip of the medical device, a graphic annotation of the current magnetic field direction 116 could be projected onto the live Fluoroscopy Image display as a steering reference. Where a localization system for determining the position of the medical device in a frame of reference translatable to the displayed image of the Fluoroscopy system is also included, a graphical rendition of portions of the medical device as determined from the localization information obtained from the localization system can be overlaid on the X-ray image display. Rates of change of control variables such as the magnetic field, or the rate of movement of the medical device may also be determined and displayed on the X-ray image display.

A graphical representation of a virtual medical device 112 can be overlaid to show a visual reference the medical device 100 being rotated or moved before initiating actual movement of the medical device. A mathematical model of the medical device can be used to define the configuration of the virtual medical device 112, which can model the behavior of the device relative to a desired navigation rotation to predict movement of the medical device 110. Thus, a desired rotation or re-orientation of the tip of the medical device 110 may be evaluated through a visual representation of a virtual medical device 112 in advance of re-orientation of the actual medical device 110. The model of the virtual medical device 112 can account for the deflective behavior of the medical device 110 relative to changes in navigation control variables such as the applied magnetic field direction, and can provide a representation of the resulting changes in configuration of the device. A graphic indication 114 of a direction for steering the medical device within the plane of the X-ray image may also be graphically overlaid onto the display for coordination with a joystick that is mapped to the X-ray plane. Likewise, a desired target such as location point 102 may be entered, and the model of the virtual medical device 112 configuration can be used to determine the appropriate change in navigation control variables to steer the tip of the medical device to the desired target destination 102.

The imaging display of the present invention may be further augmented by the use of gated location data, for example where the gating is performed with respect to ECG (electro cardiograph) data, so that the device location is always measured at the same phase of a periodic cycle of anatomical motion such as the cardiac cycle. In a preferred embodiment, this data is input into the navigation system together with the real-time location data in a manner such that the location data may be projected onto the X-ray image display.

It should be noted that the overlay of the medical device and various objects could be controlled by a user input from an input device such as a joystick, mouse, or hand-held localized stylus, or it could automatically be controlled by a computer. Alternatively, a joystick could also be used to control the direction or steering of the medical device within the subject body. Additional design considerations such as the above modifications may be incorporated without departing from the spirit and scope of the invention. More particularly, the system and method may be adapted to medical device guidance and actuation systems other than magnetic navigation systems, including electrostrictive, mechanical, hydraulic, or other actuation technologies. Likewise, a variety of medical devices such as catheters, cannulas, guidewires, microcatheters, endoscopes and others known to those skilled in the art can be remotely guided according to the principles taught herein. Accordingly, it is not intended that the invention be limited by the particular form described above, but by the appended claims.

Operation

In operation, the imaging system of the various embodiments of the present invention display an image of an operating region together with an overlay of representations of various objects in the operating region to facilitate the user's orientation within the image. For example these objects can include points that the user has identified or marked, or which have been identified or marked for the user. The objects can alternatively or additionally include shapes, for example closed loops identifying openings in the operating region. The objects can also be reconstructions of medical devices in the operating region, based upon mathematical models of the devices or position information from a localization system. The positions and shapes of the representations automatically change as the imaging plane changes when the imaging beam and imaging plate move about the operating region. Thus the user does not lose the points of reference and landmarks that he or she may have been using prior to the reorientation of the imaging system. This reorientation can occur frequently during medical procedures as the imaging system is moved to accommodate other equipment in the procedure room (e.g. a magnetic navigation system), or when the user desires a different imaging angle to better observe the procedure.

In one embodiment the imaging system consists of an imaging beam source, an imaging plate, an imaging processor, for processing the imaging data collected by the imaging plate, and a display for displaying the image from the processed imaging data. This imaging system can be used in conjunction with another system, such as a navigation system for orienting the a medical device in the operating region in the subject, or a medical localization system for determining the location of a medical device in the operating region in the subject. Whether using the navigation system or the localization system, the user can generally identify points of interest, for example anatomical land marks or points of physiological interest. Representations of these points can be displayed on the image of the operating region from the imaging system, to help the user visualize the operating region and the procedure. However, in addition to overlaying the representation on a static image from the imaging system, the overlay can be dynamically adjusted as the imaging plane changes so that the objects not only remain on the display, but the remain in the correct position and orientation relative to the displayed image and the displayed image changes.

Figure 4A:
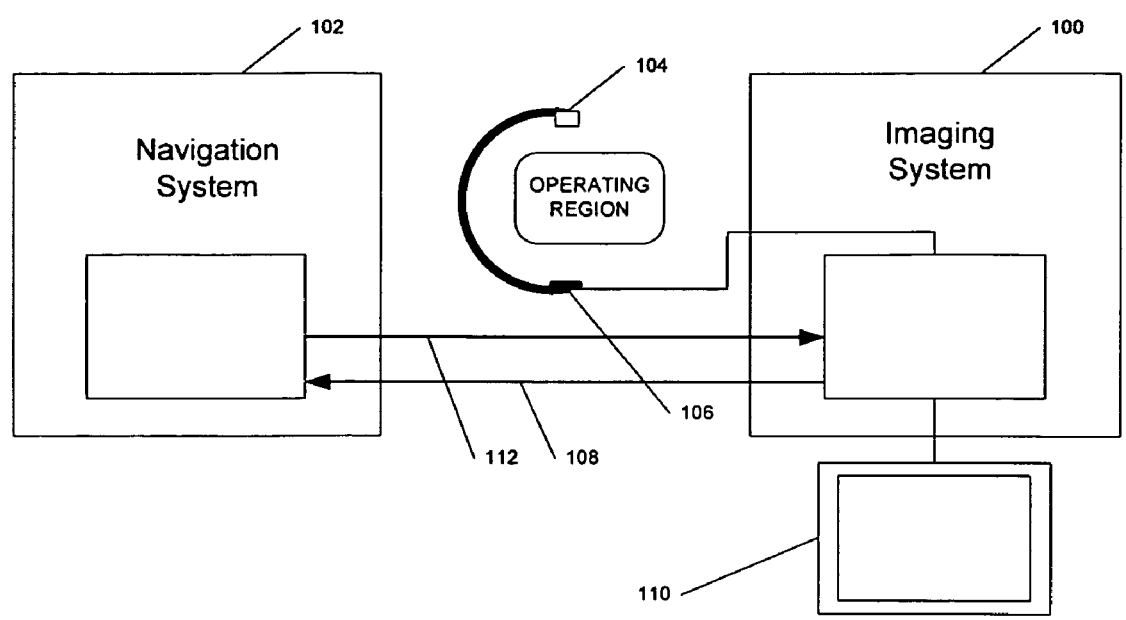
FIG. 4A is a schematic diagram of a navigation system and imaging system combination, in which the navigation system determines the where objects in the operating region should appear based upon information from the imaging system.
Figure 4B:
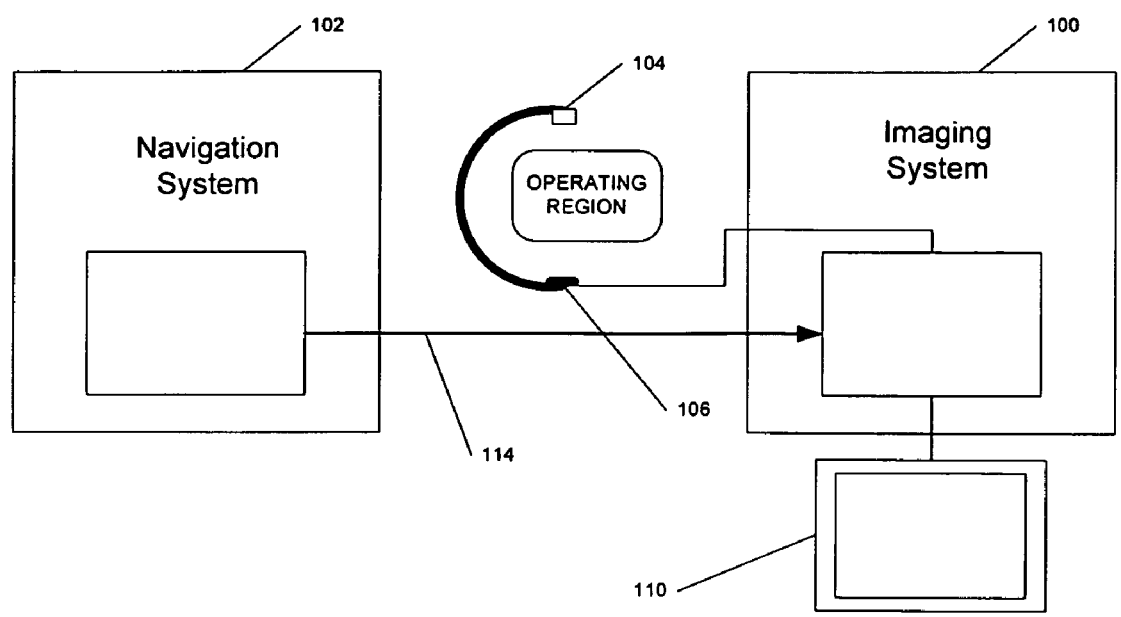
FIG. 4B is a schematic diagram of a navigation system and imaging system combination, in which the imaging system determines where objects in the operating region should appear based upon position information from the navigation system.

The method can be implemented in several ways as illustrated by FIGS. 4A and 4B. In one embodiment, shown schematically in FIG. 4A, the navigation or localization system receives information about the location of the imaging beam source and the imaging receiver, and uses this information to determine where objects of known locations in the operating region should appear on the image generated by the imaging system. More specifically, the imaging system 100 can provide the navigation system (or localization system) 102 with information about the position/orientation of the imaging beam source 104 and the imaging receiver 106. (This is represented by arrow 108). Using this information the navigation system (or localization system) 104 can determine where an object of known position in the operating region should appear in an image generated by the imaging system. This information can be communicated back to the imaging system 100 so that the selected objects can be overlaid in the proper location and orientation on the image generated by the imaging system, and displayed on the display 110. (This is represented by arrow 112)

As the imaging beam source 104 and imaging receiver 106 move, the information provided by the imaging system to the navigation system (or the localization system), and the resulting information provided by the navigation system (or the localization system) to the imaging system is updated. (This is represented by arrow 114). So that representations of the selected objects can be overlaid on the images from the imaging system are updated as the imaging system moves about the operating region.

As shown in FIG. 4B, the navigation system (or the localization system) 102 can provide the imaging system with the positions of objects in the operating region. The imaging system 100 can use this information to determine where the objects should appear in an image generated by the imaging system, using the known position of the imaging beam source 104 and imaging receiver 106, and then overlay representations of the objects on the image generated by the imaging system on the display 110.

As the positions of the imaging beam source and imaging receiver change, the imaging system can redetermine where the objects should appear in an image generated by the system in the new configuration, and overlay the representations of the object on the image generated by the imaging system, so that the representations of the objects are updated as the imaging system moves about the operating region.

Figure 5:
FIG. 5 is a view of the screen of a magnetic navigation system, with imported images from an imaging system in accordance with the principles of this invention.
Figure 6A:
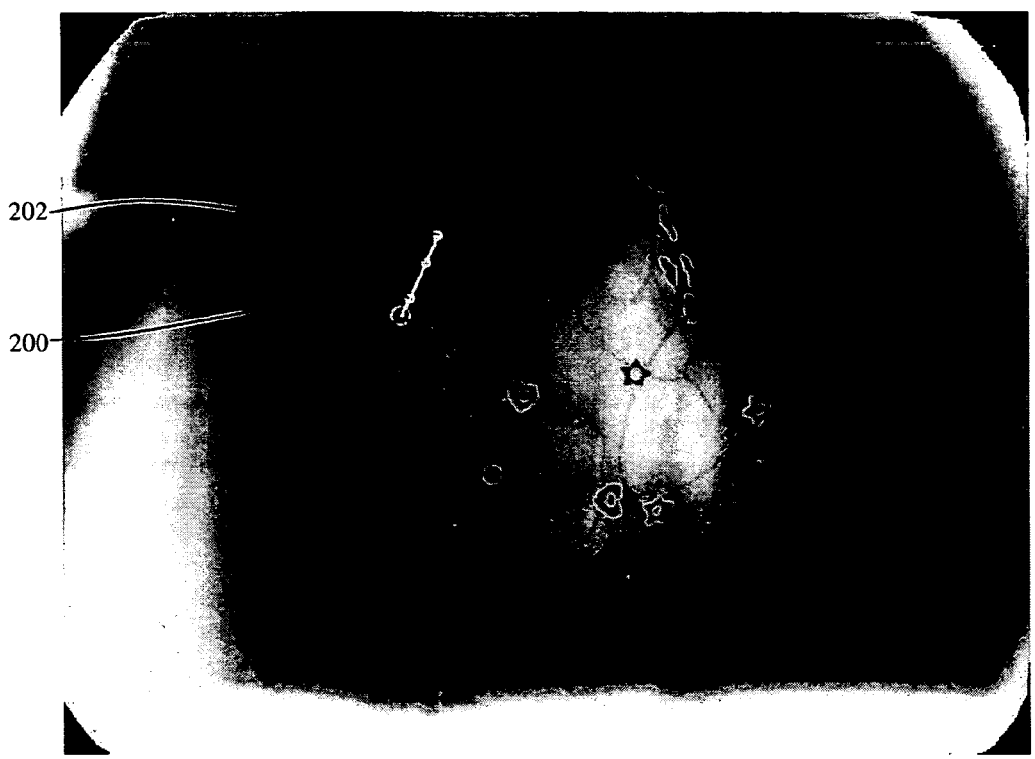
FIG. 6A is an x-ray image of an anatomic model of a human heart along an axis 26° on the LAO side, showing objects overlaid on the image in accordance with the principles of operation.
Figure 6B:
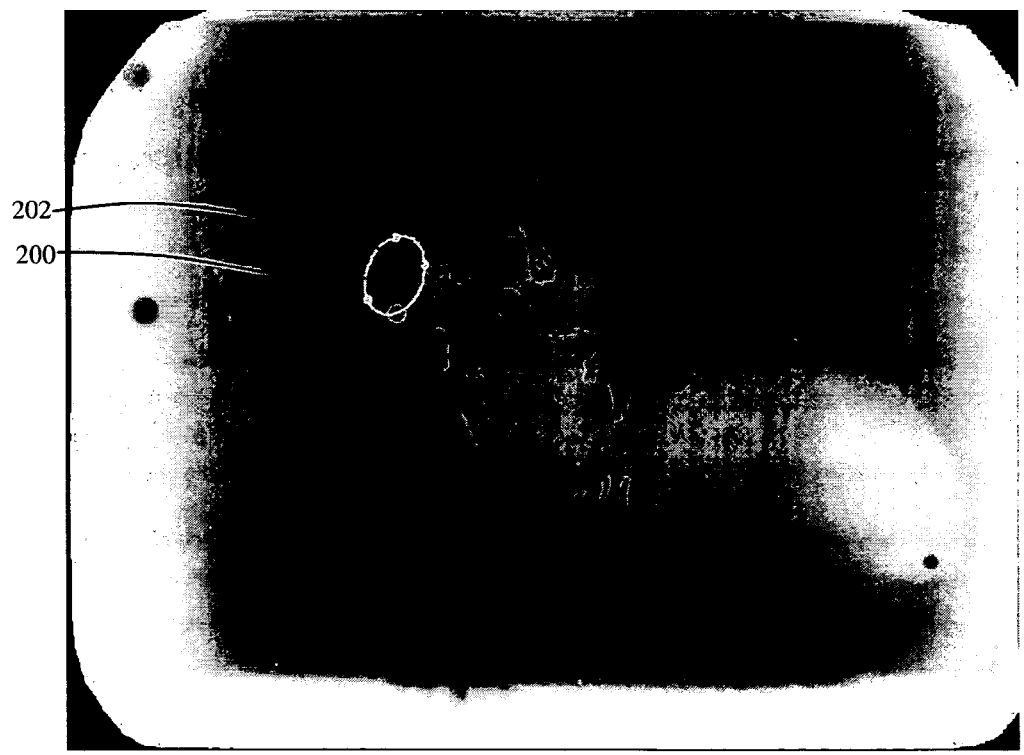
FIG. 6B is an x-ray image of the anatomic model of the human heart along an axis 26° on the RAO side.

An example of a display from a graphical user interface from a magnetic navigation system is shown in FIG. 5. The interface in FIG. 5 allows the user to import images from an x-ray imaging system, and display them in windows in the display. The magnetic navigation system allows the user to identify points in the operating region and show these points on an overlay on the image from the imaging system. The overlay becomes "persistent" such that as the imaging system is moved about the operating region, and another image is made of the operating region, the overlay is adjusted in position and/or orientation so that it correctly shows the points on the new image. This is illustrated in FIG. 5 in which two images from the operating region in different directions are depicted in side by side panes on the interface, and the overlaid objects are properly positioned and oriented in each, FIG. 6A shows an x-ray image of an anatomical model of a human heart taken in a direction 26° to the left anterior side. An object, and more specifically a representation of a ring 200 constructed from a plurality of points 202 is overlaid on the x-ray image. FIG. 6B shows an x-ray image of the anatomical model taken in a direction 26° to the right anterior side (i.e., rotated 52° from FIG. 6A). The representation of the ring 200 and constituent points 202 in FIG. 6B have been rotated from FIG. 6A in accordance with the principles of this invention, to remain in the proper orientation with respect to the image in the new imaging direction.

Figure 7A:
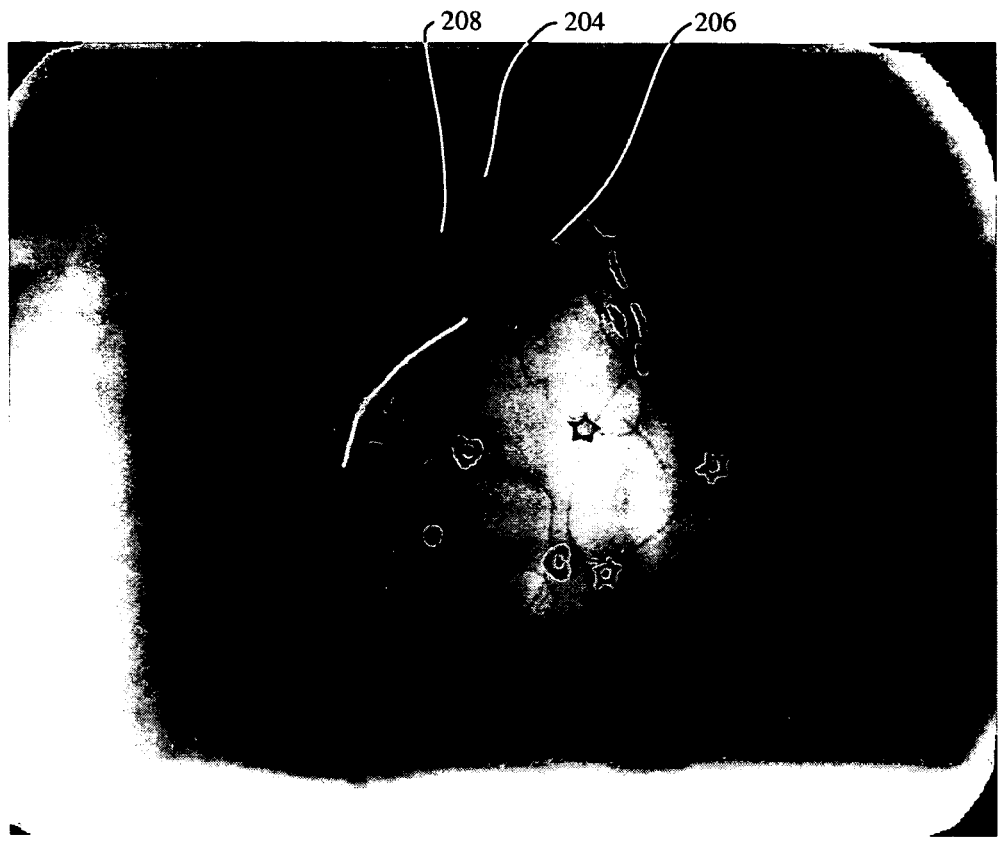
FIG. 7A is an x-ray image of an anatomic model of a human heart along an axis 25° on the LAO side, showing objects overlaid on the image in accordance with the principles of operation.

FIG. 7A shows an x-ray image of an anatomical model of a human heart taken in a direction 25° to the left anterior side.

Figure 7B:
FIG. 7B is an x-ray image of the anatomic model of the human heart along an axis 27° on the RAO side.

Objects, and more specifically a plurality of annotations including an "E" 204, an "F" 206, and a "G" 208 are overlaid on the x-ray image. FIG. 7B shows an x-ray image of the anatomical model taken in a direction 27° to the right anterior side (i.e., rotated 52° from FIG. 7A). The representation of the annotations "E" 204, "F" 206, and "G" 208 in FIG. 7B have been rotated from FIG. 7A in accordance with the principles of this invention, to remain in the proper orientation with respect to the image in the new imaging direction.

Figure 8A:
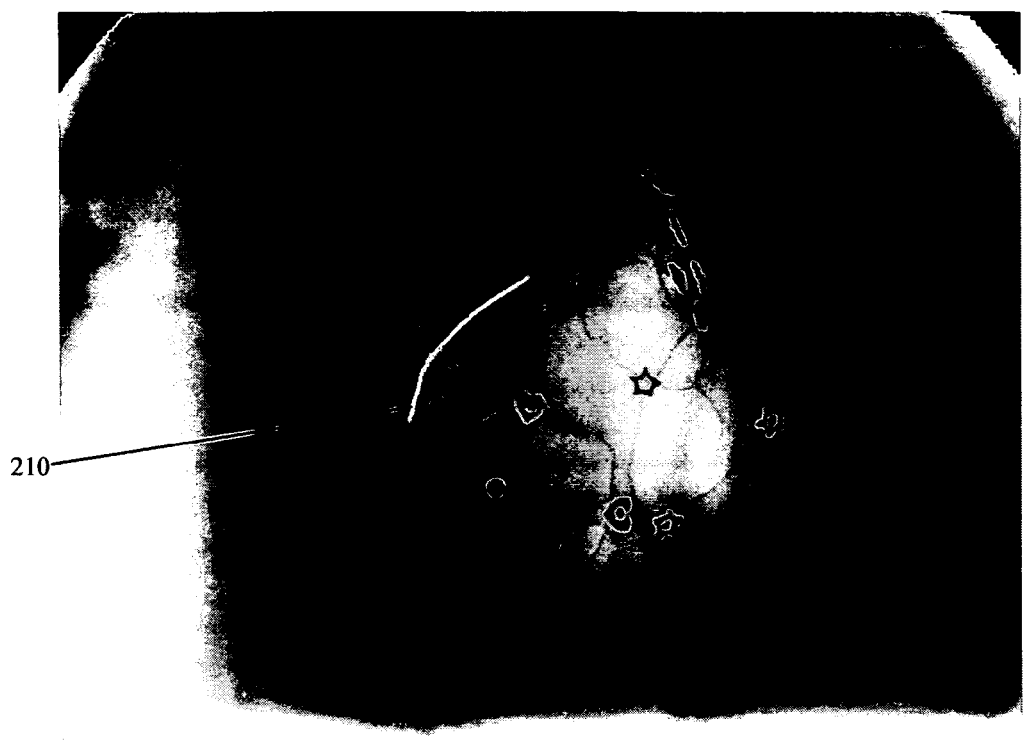
FIG. 8A is an x-ray image of an anatomic model of a human heart along an axis 25° on the LAO side, showing objects overlaid on the image in accordance with the principles of operation.

FIG. 8A shows an x-ray image of an anatomical model of a human heart taken in a direction 25° to the left anterior side. An object, and more specifically a catheter 210 is overlaid on the x-ray image. The representation of catheter 210 can be generated from localization data of one or more points on the corresponding real catheter in the operating region. Alternatively, the representation of the catheter 210 can be generated from a mathematical model of the actual catheter in the operating region (for example using the control variable from the navigation system).

Figure 8C:
FIG. 8C is an x-ray image of the anatomic model of the human heart along an axis 27° on the RAO side.
Figure 8B:
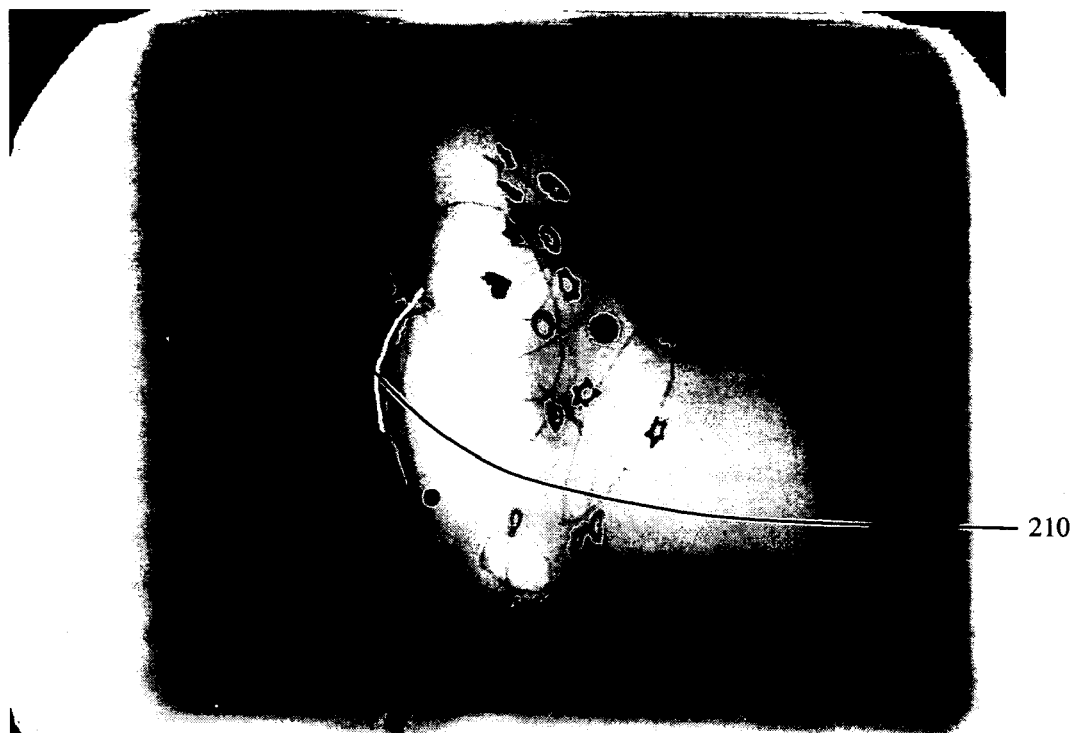
FIG. 8B is an x-ray image of the anatomic model of the human heart along an axis 8° on the RAO side.

FIG. 8B shows an x-ray image of the anatomical model taken in a direction 8° to the right anterior side (i.e., rotated 33° from FIG. 8A). The representation of the catheter 210 in FIG. 8B has been rotated from FIG. 8A in accordance with the principles of this invention, to remain in the proper orientation with respect to the image in the new imaging direction. FIG. 8C shows an x-ray image of the anatomical model taken in a direction 27° to the right anterior side (i.e., rotated 19° from FIG. 8B). The representation of the catheter 210 in FIG. 8C has been rotated from FIG. 8B in accordance with the principles of this invention, to remain in the proper orientation with respect to the image in the new imaging direction.

Figure 9B:
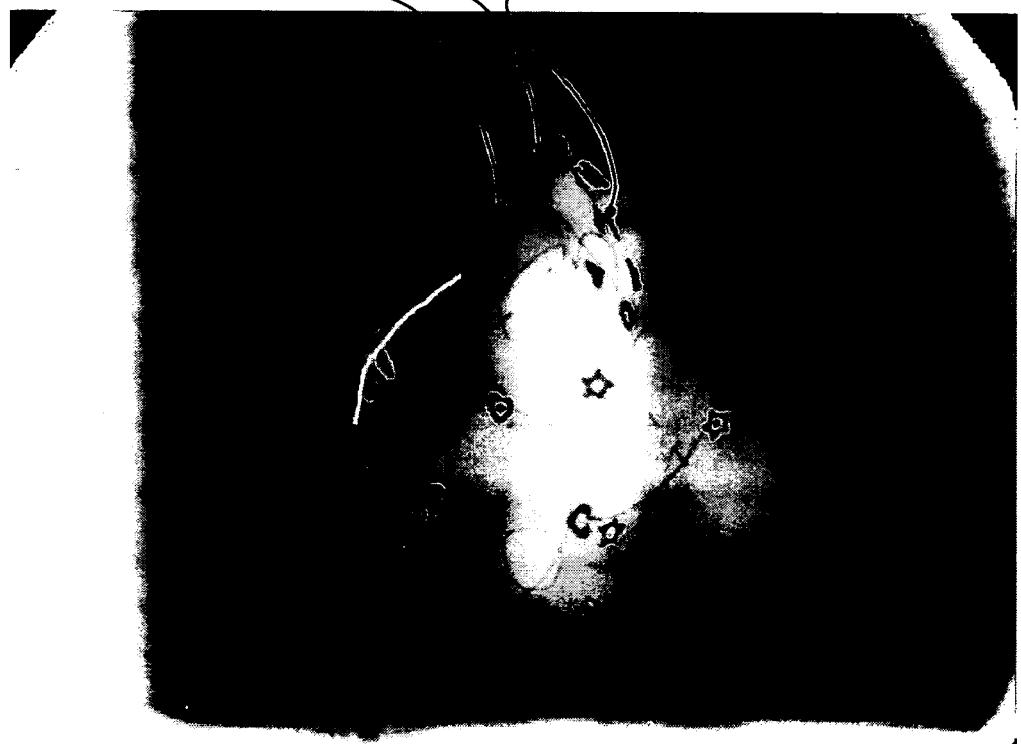
FIG. 9B is an x-ray image of an anatomic model of a human heart along an axis 16° on the LAO side.
Figure 9A:
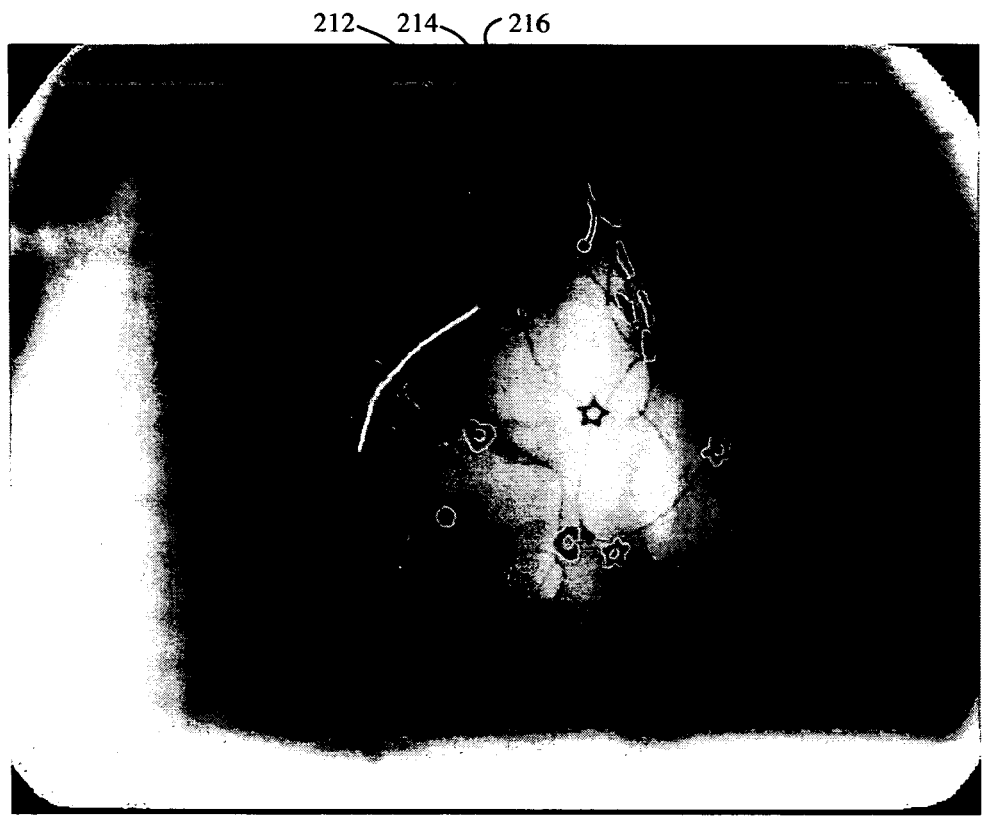
FIG. 9A is an x-ray image of an anatomic model of a human heart along an axis 25° on the LAO side, showing objects overlaid on the image in accordance with the principles of operation.
Figure 9C:
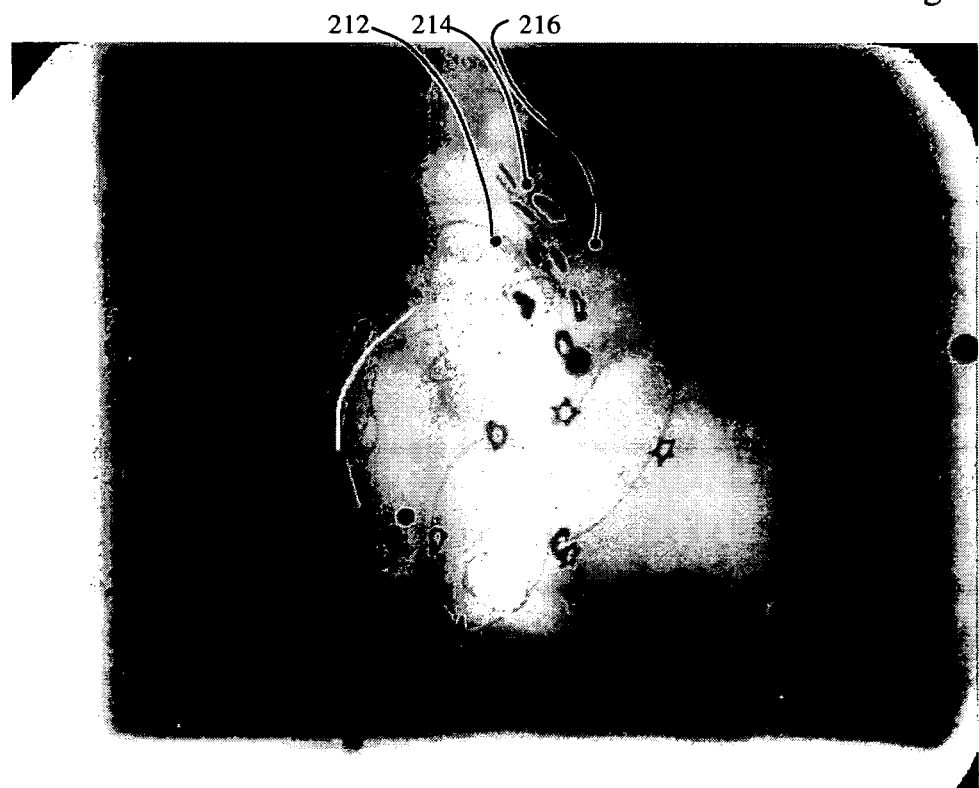
FIG. 9C is an x-ray image of an anatomic model of a human heart along an axis 6° on the LAO side.
Figure 9D:
FIG. 9D is an x-ray image of an anatomic model of a human heart along an axis 17° on the RAO side.
Figure 9E:
FIG. 9E is an x-ray image of an anatomic model of a human heart along an axis 27° on the RAO side.

FIG. 9A shows an x-ray image of an anatomical model of a human heart taken in a direction 25° to the left anterior side. Objects, and more specifically representations of points 212, 214, and 216 in the operating region are overlaid on the x-ray image. FIG. 9B shows an x-ray image of the anatomical model taken in a direction 16° to the right anterior side (i.e., rotated 9° from FIG. 9A). The representation of the points 212, 214 and 216 in FIG. 8B have been rotated from FIG. 9A in accordance with the principles of this invention, to remain in the proper orientation with respect to the image in the new imaging direction. FIG. 9C shows an x-ray image of the anatomical model taken in a direction 6° to the left anterior side (i.e., rotated 3° from FIG. 9B). The representation of the points 212, 214, and 216 in FIG. 9C has been rotated from FIG. 9B in accordance with the principles of this invention, to remain in the proper orientation with respect to the image in the new imaging direction. FIG. 9D shows an x-ray image of the anatomical model taken in a direction 17° to the right anterior side (i.e., rotated 23° from FIG. 9C). The representation of the points 212, 214, and 216 in FIG. 9D has been rotated from FIG. 9C in accordance with the principles of this invention, to remain in the proper orientation with respect to the image in the new imaging direction. FIG. 9E shows an x-ray image of the anatomical model taken in a direction 27° to the right anterior side (i.e., rotated 10° from FIG. 9D). The representation of the points 212, 214, and 216 in FIG. 9E has been rotated from FIG. 9D in accordance with the principles of this invention, to remain in the proper orientation with respect to the image in the new imaging direction.

What is claimed is:

1. A medical imaging system for imaging an operating region in a subject, the system comprising an imaging beam source, an imaging plate, and a display for displaying an image generated by the imaging beam on the imaging plate together with an overlay of at least one object in the operating region, wherein the system is configured to generate an overlay from the position of the object, the position of the imaging beam source, and the position and orientation of the imaging plate, wherein the location of where an overlay of the projected object is to appear on the display is determined in part based on the location of the imaging beam source and the location of the imaging plate, such that for any object in three-dimensional space a corresponding projected object may be suitably overlayed on the display.

2. The medical imaging system according to claim 1 wherein the object is at least one point in the operating region.

3. The medical imaging system according to claim 1 wherein the object is a loop comprising a plurality of points in the operating region.

4. The medical imaging system according to claim 1 wherein the object is a medical device in the operating region.

5. The medical imaging system according to claim 1 wherein the position of the medical device in the operating region is determined by a localization system.

6. The medical imaging system according to claim 1 wherein the position of the medical device is calculated using a mathematical model of the medical device.

7. The medical imaging system according to claim 1 wherein the imaging beam source and the imaging plate are movable about the operating region, and wherein the display updates both the displayed image and the overlay as the positions of the imaging beam and imaging plane change.

8. A method of providing medical images of an operating region in a subject's body, the method comprising: generating an image of the operating region using an imaging beam source and an imaging plate; and displaying the generated image together with an overlay of at least one object in the operating region, the overlay generated from the position of the object, the position of the imaging beam source, and the position and orientation of the imaging plate, wherein the location of where an overlay of the projected object is to appear on the display is determined in part based on the location of the imaging beam source and the location of the imaging plate, such that for any object in three-dimensional space a corresponding projected object may be suitably overlayed on the display.

9. The medical imaging system according to claim 8 wherein the object is at least one point in the operating region.

10. The medical imaging system according to claim 8 wherein the object is a loop comprising a plurality of points in the operating region.

11. The medical imaging system according to claim 8 wherein the object is a medical device in the operating region.

12. The medical imaging system according to claim 8 wherein the position of the medical device in the operating region is determined by a localization system.

13. The medical imaging system according to claim 8 wherein the position of the medical device is calculated using a mathematical model of the medical device.

14. The method according to claim 8 wherein the imaging beam source and the imaging plate are movable about the operating region, and further comprising updating the both the displayed image and the overlay as the positions of the imaging beam and imaging plane change.

15. A medical imaging and display system for displaying medical images of an operating region in a subject, the system comprising: a localization system for determining the location of an object in the operating region; an imaging system having an imaging beam source, an imaging plate, and a display for displaying an image of the operating region generated by the imaging beam source and the imaging plate, together with an overlay of at least one object in the operating region, wherein the system is configured to generate an overlay from the position of the object, the position of the imaging beam source, and the position and orientation of the imaging plate, wherein the location of where an overlay of the projected object is to appear on the display is determined in part based on the location of the imaging beam source and the location of the imaging plate, such that for any object in three-dimensional space a corresponding projected object may be suitably overlayed on the display.

16. The medical imaging and display system according to claim 15 wherein the imaging system communicates the position of the imaging beam source and the imaging plate to the localization system, and the localization system calculates the position of the object on the display.

17. The medical imaging and display system according to claim 15 wherein the localization system communicates the position of the object in the operating region to the imaging system, and the imaging system calculates the position of the object on the display.

18. The medical imaging system according to claim 15 wherein the object is at least one point in the operating region.

19. The medical imaging system according to claim 15 wherein the object is a loop comprising a plurality of points in the operating region.

20. The medical imaging system according to claim 15 wherein the object is a medical device in the operating region.

21. The medical imaging system according to claim 15 wherein the position of the medical device in the operating region is determined by a localization system.

22. The medical imaging system according to claim 15 wherein the position of the medical device is calculated using a mathematical model of the medical device.

23. A method of displaying medical images of an operating region in a subject, the method comprising the steps of: generating an image of the operating region using an imaging beam source and an imaging plate; displaying the generated image; determining the location relative to the generated image of an object in the operating region based upon the position of the object in the operating region, the location of the imaging beam source, and the location of the imaging beam plate; overlaying a representation of the object on the display to position an overlay of at least one object in the operating region; wherein the location of where an overlay of the projected object is to appear on the display is determined in part based on the location of the imaging beam source and the location of the imaging plate, such that for any object in three-dimensional space a corresponding projected object may be suitably overlayed on the display.

24. A system for navigating a medical device in a body, having a display means for displaying an image of an operating region in the body, the navigation system comprising: a means of remotely actuating the medical device for navigational purposes; a connection to an anatomical imaging system, wherein image information can be transferred to the navigation system for viewing on the display means; a means for transfer of imaging parameters including the location of an imaging beam source and an imaging plate associated with the imaging system to the navigation system; a means of transformation of three dimensional geometrical information corresponding to a location in space, based on the imaging parameters including the location of an imaging beam source and an imaging plate; and a means of transferring the suitably transformed geometrical information to the imaging system for display on its live imaging monitor, wherein the transformation of the three-dimensional information corresponding to a location in space is determined in part based on the location of the imaging beam source and the location of the imaging plate, such that for any three-dimensional location in space a corresponding projected location within an image being displayed may be determined.

25. The system of claim 24, where the imaging parameters include positions of mechanisms of an X-ray C-arm system.

26. The system of claim 24, where the geometrical information is the real-time location and orientation of a localized medical device.

27. The system of claim 24, further comprising a graphic overlay of at least one target location that is suitably projected onto the anatomical image shown on the live imaging display.

28. The system of claim 24, further comprising a graphic overlay of at least one reference location that is suitably projected onto the anatomical image shown on the live imaging display.

29. The system of claim 23, wherein the current location and orientation of the medical device is continuously updated and graphically overlaid onto the anatomical image shown on the live imaging display.

30. The system of claim 24, further comprising a mathematical model of a predicted configuration of the medical device that is suitably projected onto the live imaging display, wherein the mathematical model provides a visual reference of a predicted location and orientation of the medical device that corresponds to a desired change in control variables.

31. The system of claim 24, further comprising a mathematical model of a predicted configuration of the medical device that is suitably projected onto the live imaging display, wherein the mathematical model provides a visual reference of a predicted location and orientation of the medical device that corresponds to a change in control variables.

32. The system of claim 29, wherein the current location and orientation of the medical device is graphically displayed together with other geometrical information in the live imaging display.

33. The system of claim 29, wherein the geometrical information transferred to and displayed on the live imaging display is obtained from a three dimensional pre-operative image dataset.

34. The system of claim 29, wherein the current location and orientation of the medical device is graphically displayed in the live imaging display together with data from a three dimensional intra-operative surface image rendering.

35. The system of claim 24, further comprising data input from a source of anatomical surface normal information, wherein the surface normal information is transformed to the frame of reference of the displayed live image, and is graphically overlaid onto the anatomical image shown on the live imaging display.

36. The system of claim 24, wherein the surface normal information is transformed using an orthographic projection matrix incorporating a source to image distance variable.

37. The method of claim 24, where the geometrical information comprises anatomical landmarks.

38. The method of claim 24, where the geometrical information comprises anatomical curvilinear features.

39. The method of claim 24, where the geometrical information comprises anatomical surface portions.

40. The method of claim 24, where the geometrical information comprises reconstructed vascular path data.

41. An improved system for remotely navigating a medical device in a body, having a display device for displaying an image of the medical device in the operating region, the improvement comprising: a means of remote actuation of the medical device; a means of controlling the remote actuation of the medical device from the navigation system; transfer of real-time location data to the navigation system from a localization system for determining the position of the medical device; a connection to an X-ray imaging system, wherein imaging parameters including the location of an imaging beam source and an imaging plate can be transferred to the navigation system from the imaging system, and said navigation system is configured to transform said real-time location data for the position of the medical device into a projection point, determined in part based on the location of the imaging beam source and the location of the imaging plate; and wherein geometrical information relating to said projection point can be transferred from the navigation system to the imaging system so that for any real-time location of the medical device a corresponding projection point may be suitably located on the live imaging display device, such that a continuously updated current location and orientation of the medical device as determined by the localization system are suitably projected and graphically overlaid onto the live X-ray image.

42. The system of claim 41, wherein a graphic overlay of at least one target location is suitably projected and overlaid onto the live X-ray image display.

43. The system of claim 41, wherein a graphic overlay of at least one reference location is suitably projected and overlaid onto the live X-ray image display.

44. The system of claim 41, wherein at least one user-defined device marker is projected and graphically overlaid onto the live X-ray image display.

45. The system of claim 41, further comprising a mathematical model of the configuration of the medical device that is suitably projected onto the live X-ray image display, wherein the mathematical model provides a visual reference of a predicted location and orientation of the medical device that corresponds to a desired change in control variables.

46. The system of claim 41, further comprising a mathematical model of the configuration of the medical device that is suitably projected onto the live X-ray image display, wherein the mathematical model provides a visual reference of a predicted location and orientation of the medical device that corresponds to a change in control variables.

47. The system of claim 41, wherein the current location and orientation of the medical device is graphically displayed on the live X-ray image display together with data obtained from a three dimensional pre-operative image dataset.

48. The system of claim 41, wherein the current location and orientation of the medical device is graphically displayed on the live X-ray image display together with data obtained from a three dimensional intra-operative surface image dataset.

49. The system of claim 41, further comprising data input from a source of anatomical surface normal information, wherein the surface normal information is graphically overlaid onto the live X-ray image display.

50. The system of claim 49, wherein the surface normal information is transformed using an orthographic projection matrix incorporating a source to image distance variable.

51. The method of claim 41, where the geometrical information comprises anatomical landmarks.

52. The system of claim 41, where the geometrical information comprises anatomical curvilinear features.

53. A system for remotely navigating a medical device in a body with a remote navigation system having a display for displaying an image of operating region, the system comprising: a means of controlling the remote actuation of the medical device from the navigation system; a connection to an X-ray imaging system, wherein X-ray imaging parameters including the location of a X-ray beam source and an X-ray plate associated with the X-ray imaging system can be transferred to the navigation system from the imaging system; a means of transforming three dimensional geometrical information relating to a known point into a projection point for appropriate projection and overlay, wherein the transformation of the three-dimensional geometrical information is determined in part using the X-ray imaging parameters of the location of the imaging beam source and the location of the imaging plate; and wherein the system is configured for displaying the transformed geometrical information on the live X-ray imaging display.

54. The system of claim 53, where the geometrical information comprises anatomical landmarks.

55. The system of claim 53, where the geometrical information comprises reference positions.

56. The system of claim 53, where the geometrical information comprises target locations.

57. The system of claim 53, where the geometrical information comprises predicted device configurations.

58. The system of claim 53, where the geometrical information comprises real-time device location and orientation data.

59. The system of claim 53, where the geometrical information comprises anatomical curvilinear features.

60. The system of claim 53, where the geometrical information comprises anatomical surface portions.

61. The system of claim 53, where the geometrical information comprises identified device markers.

62. The system of claim 53, where the geometrical information comprises surface normal data.

63. The system of claim 53, where the geometrical information comprises geometrical data obtained from three dimensional image data.

64. The system of claim 53, where the geometrical information comprises reconstructed vascular path data.

65. A method for overlaying geometrical information onto an X-ray imaging display for use in remotely navigating a medical device in a body, the method comprising the steps of: connecting a navigation system to an X-ray imaging system, wherein X-ray imaging parameters including the location of a X-ray beam source and an X-ray plate associated with the X-ray imaging system can be transferred to the navigation system from the imaging system; transforming three dimensional geometrical information relating to a known point into a projection point for appropriate projection and overlay, wherein the transformation of the three-dimensional geometrical information is determined in part using the X-ray imaging parameters of the location of the imaging beam source and the location of the imaging plate; displaying the transformed geometrical information relating to a protection point on the live X-ray imaging display; and controlling the remote actuation of the medical device from the navigation system using the geometrical information overlaid on the X-ray imaging display.

66. The method of claim 65, further comprising the step of providing predicted device configurations for use in controlling the actuation of the medical device.

67. The method of claim 65, wherein the geometrical information comprises anatomical landmarks.

68. The method of claim 65, wherein the geometrical information comprises reference positions.

69. The method of claim 65, wherein the geometrical information comprises target locations.

70. The method of claim 65, wherein the geometrical information comprises real-time device location and orientation data.

71. The system of claim 53 wherein the location of where the projected object is to appear as an overlay on the display is determined based on the distance h between the location of the imaging plate and the object in three-dimensional space, and the distance d between the imaging plate and the imaging beam source in three-dimensional space.

72. The method of claim 65 wherein the transforming of three dimensional geometrical information relating to a known point into a projection point for overlay on a display is determined based on the distance h between the location of the imaging plate and the object in three-dimensional space, and the distance d between the imaging plate and the imaging beam source in three-dimensional space.

* * * * *